United States Patent
Steinke et al.

(10) Patent No.: US 9,841,337 B2
(45) Date of Patent: Dec. 12, 2017

(54) PRESSURE DETERMINATION FOR HPLC APPLICATIONS

(71) Applicant: Agilent Technologies, Inc., Santa Clara, CA (US)

(72) Inventors: Armin Steinke, Ettlingen (DE); Christian Daniel Ruf, Karlsbad (DE)

(73) Assignee: Agilent Technologies, Inc., Santa Clara, CA (US)

( * ) Notice: Subject to any disclaimer, the term of this patent is extended or adjusted under 35 U.S.C. 154(b) by 13 days.

(21) Appl. No.: 14/907,786

(22) PCT Filed: Jul. 26, 2013

(86) PCT No.: PCT/IB2013/056151
§ 371 (c)(1),
(2) Date: Jan. 26, 2016

(87) PCT Pub. No.: WO2015/011530
PCT Pub. Date: Jan. 29, 2015

(65) Prior Publication Data
US 2016/0169757 A1    Jun. 16, 2016

(51) Int. Cl.
*G01L 7/02* (2006.01)
*G01L 9/00* (2006.01)
(Continued)

(52) U.S. Cl.
CPC .......... *G01L 9/0027* (2013.01); *B01L 3/5027* (2013.01); *G01N 30/32* (2013.01);
(Continued)

(58) Field of Classification Search
None
See application file for complete search history.

(56) References Cited

U.S. PATENT DOCUMENTS

| 3,985,021 A | 10/1976 | Achener et al. |
| 4,982,597 A | 1/1991 | Berger |

(Continued)

FOREIGN PATENT DOCUMENTS

| CN | 2881628 | 3/2007 |
| EP | 0309596 A1 | 9/1987 |

(Continued)

OTHER PUBLICATIONS

M.J. Kohl, S.I. Abdel-Khalik, S.M. Jeter, Di. Sadowsk,"A microfluidic experimental platform with internal pressure measurements", Sensorsand Actuators A 118 (2005), pp. 212-221.

(Continued)

*Primary Examiner* — Andre Allen

(57) ABSTRACT

Disclosed is a pressure determining unit configured for determining a pressure of a fluid. The pressure determining unit comprises a body structure and a deformation detector. The body structure has a fluidic path configured for conducting the fluid, wherein the body structure has a first surface in a first dimension and in a second dimension, and a thickness in a third dimension. The deformation detector is configured for responding to an elongation into the second dimension of the first surface of the body structure by generating a signal indicative of a value of the pressure of the fluid in the body structure. The fluidic path of the body structure comprises one or more first channel segments, each first channel segment having a height into the third dimension being at least twice of its width into the second dimension.

18 Claims, 7 Drawing Sheets

(51) Int. Cl.
　　*B01L 3/00*　　(2006.01)
　　*G01N 30/32*　　(2006.01)
　　*G01N 30/60*　　(2006.01)

(52) U.S. Cl.
　　CPC . *B01L 2200/146* (2013.01); *B01L 2300/0627* (2013.01); *B01L 2300/0816* (2013.01); *B01L 2300/14* (2013.01); *B01L 2400/0487* (2013.01); *G01N 30/6095* (2013.01)

(56) References Cited

U.S. PATENT DOCUMENTS

| | | | |
|---|---|---|---|
| 5,645,684 | A | 7/1997 | Keller |
| 7,252,006 | B2 | 8/2007 | Tai et al. |
| 7,509,869 | B2 | 3/2009 | Liu et al. |
| 2004/0154383 | A1 | 8/2004 | Woolf et al. |
| 2009/0238722 | A1 | 9/2009 | Mora-Fillat et al. |
| 2013/0133760 | A1* | 5/2013 | Bunner .............. G01N 30/32 137/488 |
| 2013/0145853 | A1 | 6/2013 | Donzier et al. |
| 2015/0000416 | A1* | 1/2015 | Baeuerle ............ B01L 3/5027 73/708 |
| 2016/0363499 | A1* | 12/2016 | Kelly .................. G01L 9/0051 |

FOREIGN PATENT DOCUMENTS

| | | |
|---|---|---|
| EP | 1577012 A1 | 4/2005 |
| JP | 2008032523 A | 2/2008 |
| JP | 2008286802 A | 11/2008 |
| JP | 2013527424 A | 6/2013 |
| JP | 2013528801 A | 7/2013 |
| WO | 2007014336 A1 | 2/2007 |
| WO | 2011013111 A2 | 2/2011 |
| WO | 2011143268 A1 | 11/2011 |
| WO | 2013037414 A1 | 3/2013 |

OTHER PUBLICATIONS

Search Report and Written Opinion dated Feb. 4, 2014, from related PCT Application No. PCT/IB2013/056151.
Japanese Office action dated May 18, 2017 from related Japanese Application No. 2016-528609.

* cited by examiner

PRESSURE DETERMINATION FOR HPLC APPLICATIONS

RELATED APPLICATIONS

This application is the national stage of International Application No. PCT/IB2013/056151, filed Jul. 26, 2013, titled "PRESSURE DETERMINATION FOR HPLC APPLICATIONS," the content of which is incorporated herein by reference in its entirety.

BACKGROUND ART

The present invention relates to pressure determination, in particular in a high performance liquid chromatography application.

Many technical fields require pressure measurement, e.g. as disclosed in U.S. Pat. Nos. 3,985,021, 5,645,684, DE 19832681, U.S. Pat. No. 7,252,006, WO 2007/014336, U.S. Pat. No. 7,509,869, WO 2011/013111, M. J. Kohl, S. I. Abdel-Khalik, S. M. Jeter, D. L. Sadowski, "A microfluidic experimental platform with internal pressure measurements", Sensors and Actuators A 118 (2005), pages, 212 to 221, or US 2009/238722

In high performance liquid chromatography (HPLC), a liquid has to be provided usually at a very controlled flow rate (e. g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid (e.g. a chemical or biological mixture) with compounds to be separated is driven through a stationary phase (such as a chromatographic column packing), thus separating different compounds of the sample fluid which may then be identified. The term compound, as used herein, shall cover compounds which might comprise one or more different components.

The mobile phase, for example a solvent, is pumped under high pressure typically through a chromatographic column containing packing medium (also referred to as packing material or stationary phase). As the sample is carried through the column by the liquid flow, the different compounds, each one having a different affinity to the packing medium, move through the column at different speeds. Those compounds having greater affinity for the stationary phase move more slowly through the column than those having less affinity, and this speed differential results in the compounds being separated from one another as they pass through the column. The stationary phase is subject to a mechanical force generated in particular by a hydraulic pump that pumps the mobile phase usually from an upstream connection of the column to a downstream connection of the column. As a result of flow, depending on the physical properties of the stationary phase and the mobile phase, a relatively high pressure drop is generated across the column.

The mobile phase with the separated compounds exits the column and passes through a detector, which registers and/or identifies the molecules, for example by spectrophotometric absorbance measurements. A two-dimensional plot of the detector measurements against elution time or volume, known as a chromatogram, may be made, and from the chromatogram the compounds may be identified. For each compound, the chromatogram displays a separate curve feature also designated as a "peak". Efficient separation of the compounds by the column is advantageous because it provides for measurements yielding well defined peaks having sharp maxima inflection points and narrow base widths, allowing excellent resolution and reliable identification and quantitation of the mixture constituents. Broad peaks, caused by poor column performance, so called "Internal Band Broadening" or poor system performance, so called "External Band Broadening" are undesirable as they may allow minor components of the mixture to be masked by major components and go unidentified.

Also in liquid chromatography, pressure measurement of a fluid may be desired e.g. by applying pressure detectors. While pressure detection might be beneficial at virtually any position within the flow path, only a limited number of pressure detectors are typically applied at a few positions only within the flow path, in particular not to add additional dead volumes but also for reasons of additional costs as well as limited accuracy and applicable pressure range of most available pressure detectors.

WO 2011/143268 A1 discloses a pressure sensing and flow control in diffusion-bonded planar devices for fluid chromatography.

WO 2013/037414 A1, by the same applicant, discloses a fluidic chip device for processing a fluid. The fluidic chip device comprises a plurality of layers laminated to one another. At least a part of the layers comprises a patterned section of an alternating sequence of bars and fluidic channels for conducting the fluid under pressure. The patterned section is configured for being displaceable in response to the pressure. A pressure detector responds to the displacement of the patterned section by generating a detector signal being indicative of a value of the pressure.

DISCLOSURE

It is an object of the invention to provide an improved pressure determination, in particular for HPLC applications.

According to an embodiment of the present invention, a pressure determining unit is provided which is configured for determining a pressure of a fluid. The pressure determining unit comprises a body structure and a deformation detector. The body structure comprises a fluidic path which is configured for conducting the fluid (which is typically a liquid under pressure). The body structure has a first surface extending in a first dimension as well as in a second dimension. A thickness of the body structure extends into a third dimension. The deformation detector is configured for responding to an elongation into the second dimension of the first surface of the body structure, and generates in response to such elongation a signal indicative of a value of the pressure of the fluid in the body structure.

According to a first aspect of the present invention, the fluidic path of the body structure comprises one or more first channel segments. Each first channel segment has a height in the third dimension which is at least twice of the width of such first channel segment into the second dimension. Preferably, the height may be at least three times and more preferred at least four times of its width into the second dimension. By providing such a "slim" geometry for the respective first channel segment(s), any deformation of the channel under the influence of the fluid under pressure mainly results in a deformation (of the channel) into the second dimension thus leading to an elongation of the first surface into the second dimension, which can then be detected by the deformation detector. It is to be understood that the pressure in the channel may lead to a deformation into any direction subject in particular to the respective channel geometry as well as the specific properties of the body structure, such as material properties as well as properties resulting e.g. from manufacturing such body structure. Providing such "slim" channel geometry can lead to a deformation into the second dimension which can be significantly larger than any deformation into the third dimension. In this respect, it is to be understood that the first channel segment(s) local deformation(s) into the third dimension (height), which may occur locally above and/or below the respective channel(s), may in turn lead to a deformation into the second dimension as measured by the deformation detector, thus leading to an error in the pressure detection. By applying such slim channel geometry, the signal to noise ratio in the pressure detection of the signal provided by the deformation detector can be improved.

According to a second aspect of the present invention, the fluidic path of the body structure comprises a plurality of first channel segments. Each channel segment is oriented so that a direction of flow is substantially into the first dimension. At least two of the first channel segments are arranged in a respective row along the first dimension. A respective intermediate area is provided between neighboring channel segments arranged in a respective row, wherein the intermediate area is not part of the fluidic path. This can allow structuring or scaling a deformation profile (i.e. a profile of deformation into the second dimension along the first dimension), which may allow reducing non-linearity effects in the signal generated by the deformation detector in response to an elongation of the first surface into the second dimension. It has been found by the present inventors that providing a respective first channel segment over the entire length (in the first dimension) of a row without having a respective intermediate area (which is not part of the fluidic path and thus not being subject to deformation from within such intermediate area) may lead to a high(er) elongation in particular in a middle area along a front surface (into the second dimension) of the body structure. In particular due to non-linearities in material properties such elongation of the body structure into the second dimension may also become subject to non-linearity effects in particular with increasing pressure of the fluid (e.g. beyond 500 or 1000 bar). By providing such intermediate area in a row between neighboring channel segments and preferably in the middle or close to the middle of such row, the effect of non-linearities can be reduced and the resulting signal of the deformation detector in response to an elongation into the second dimension can exhibit a larger degree of linearity (or, in other words, is less non-linear).

A respective intermediate area can be provided or result from having two neighboring channel segments, which are fluidically coupled with each other but not over the entire channel cross section (provided into the first and third dimensions) of the neighboring channel segments. This leads to the intermediate area between the neighboring channel segments, which then is not part of the fluidic path.

In one embodiment, the fluidic path comprises a plurality of respective rows, preferably parallel rows, along the first dimension. The fluid path further comprises a plurality of second channel segments, and each second channel segment is oriented so that a direction of flow is substantially in the second dimension.

At least one of the second channel segments may penetrate through at least one intermediate area or, in other words, may be surrounded by at least one intermediate area.

In a preferred embodiment, each row along the first dimension comprises two channel segments and has a respective intermediate area between two channel segments. Each row along the first dimension is coupled by a respective second channel segment. The last row (or the first row—dependent on the order of counting) is further coupled to a respective second channel segment, and this second channel segment is surrounded by one or more respective intermediate areas of the rows. Such structure might then be a plurality of parallel rows along the first dimension coupled together by respective second channel segments with the first (or last) second channel segment in the flow path (e.g. the feeding or return path to the first channel segments) being arranged and led through the respective intermediate areas in the rows.

According to a third aspect of the present invention, the pressure determining unit further comprises a reference body structure comprising a reference fluid path configured for conducting the fluid. The reference body structure has (similar to or in accordance with the body structure) a first surface extending in a first dimension as well as in a second dimension, and has a thickness (or height) in a third dimension. The first, second, and third dimensions of the body structure and the reference body structure may not necessarily have the same spatial orientation (e.g. the first dimension of the body structure does not necessarily have to be the same or in parallel to the first dimension of the reference body structure, etc.) but are related only with respect to either the body structure or the reference body structure.

The pressure determining unit according the third aspect further comprises a reference deformation detector which is configured for responding to an elongation into the second dimension of the first surface of the reference body structure by generating a reference signal indicative of a value of the pressure of the fluid in the reference body structure. The fluidic path and the reference fluidic path are fluidically coupled with each other, e.g. the fluid path and the reference fluid path may be coupled in a serial or parallel manner so that either the fluid flows in a serial manner first through the body structure and then through the reference body structure (or vice versa) or in a parallel manner so that a partial flow is flowing through the fluidic path of the body structure and another partial flow is flowing through the reference fluidic path of the reference body structure.

Further in the pressure determining unit according to the third aspect, the reference body structure is configured to experience a pattern of variation in thickness (into the third dimension) on its first surface under the influence of a variation in pressure in the reference fluid path, which substantially matches a pattern of variation in thickness (into the third dimension) of the body structure on its first surface under the influence of a variation in pressure in the fluid path. In other words, both the reference body structure as well as the body structure are configured so that a respective pattern of variation in thickness on their respective first surfaces resulting from a variation in pressure in the respective fluid path substantially matches to each other. Accordingly, a variation in pressure in the fluid flowing through both of the body structure and the reference body structure will lead to substantially the same deformation pattern (into the third dimension) on their respective first surfaces. Such pattern of variation in thickness on the respective first surface can be understood as a three dimensional surface deformation which may locally occur beyond and/or below a respective flow path in the respective body structure. Such local deformation may result from a deformation (e.g. elongation) of the respective flow path into the respective third dimension (height) and is typically (e.g. dependent on the respective geometry and material) more or less limited locally beyond and/or below the respective flow path (e.g. channels) within the respective body structure.

Such reference body structure with substantially matching pattern on the respective first surfaces may allow reducing an effect of such pattern of variation in thickness onto the signal as provided by the deformation detector in response to an elongation into the second dimension. As discussed above, such local variation(s) in height (or thickness) of the first surface can also lead to a variation into the second dimension thus leading to an error signal or, in other words, to a reduced accuracy of the signal provided by the deformation detector. By having substantially matching patterns on the body structure as well as on the reference body structure, the accuracy of the measurement can be increased, e.g. by comparing both signals and/or jointly analyzing the resulting signals.

In one embodiment, a signal processing unit is provided for deriving a value of the pressure of the fluid by jointly analyzing the signal together with the reference signal. This might preferably be accomplished by subtracting at least a part of the reference signal from the signal (or vice versa) or by otherwise adequately combining the signals thus eliminating or at least reducing the effects resulting from variations in thickness on the respective first surfaces. Preferably, a Wheatstone bridge arrangement as readily known in the art can be used for jointly analyzing the signal together with the reference signal.

In one embodiment, the fluidic path of the body structure comprises one or more first channel segments, each first channel segment having a width into the second dimension. The reference fluidic path of the reference body structure comprises one or more first reference channel segments, each first reference channel segment having a width into the second dimension and a length into the first dimension. The width of the first channel segment substantially corresponds to the width of the first reference channel segments. This can allow to substantially match the deformation into the third dimension of both the body structure and the reference body structure.

In one embodiment, the fluidic path of the body structure comprises one or more first channel segments, each first channel segment having a height into the third dimension. The reference fluidic path of the reference body structure comprises one or more first reference channel segments, each first reference channel segment having a height into the third dimension. The height of the first channel segments is at least twice (and preferably at least three times, and more preferably at least four times) the height of the first reference channel segments. This can allow that any deformation into the second dimension of the body structure is significantly larger than of the reference body structure. The width of the first channel segment(s) substantially correspond(s) to the width of the first reference channel segment(s), so that the resulting reference signal is mainly determined by the (unwanted) deformation into the third dimension. Subtracting the reference signal from the signal (or vice versa) can significantly reduce any measurement error caused from such deformation into the third dimension.

It is clear that the aforementioned elements and embodiments of the respective aspects may also be combined and applied together in any combination, in order to further improve pressure determination in particular for HPLC applications. The following embodiments relate to each aspect as well as to each combination of the aspects.

In one embodiment, the body structure comprises a plurality of layers laminated to one another. The layers may be elongated into the first dimension as well as into the second dimension, and each layer may have a thickness into the third dimension. An expansion into the first dimension is preferably significantly smaller than an expansion into the second dimension. The respective channels may be made e.g. by cutting or etching out portions in one or more of the layers, so that the channels can be provided by the cut or etched out portions when the layers become laminated to one another (e.g. by diffusion LASER bonding).

In one embodiment, the body structure is comprised of one or more materials of a group of materials comprising: metal (preferably steel, such as stainless steel, e.g. 304L, 306L, 316L, etc.), ceramic, polymer (preferably a plastic material), a composite material, or any other adequate material. In case the body structure is comprised of layers, each layer may be comprised of at least one material of the aforementioned group of materials.

In one preferred embodiment, the body structure is provided by a plurality of metal layers, preferably joined together by diffusion or LASER bonding. The layers (e.g. metal sheets) are preferably punched and etched into shape prior to the bonding step.

In one embodiment, at least one channel segment (of the first and/or second channel segment) is comprised of a plurality of sub-channels, with the sub-channels being arranged in a parallel configuration (preferably into the third dimension) and each two neighboring sub-channels having a respective separator (preferably a membrane) in-between the sub-channels. Such arrangement may allow achieving the same or similar effect with respect to elongation into the second dimension of the body structure. The separator is preferably designed to be rather thin in the third dimension, especially in comparison to the channel dimensions. The separator may be impermeable, semipermeable or permeable. The separator should preferably be of the same or higher elasticity than the body structure. The separator separated arrangement of the sub-channels might be beneficial dependent on the manufacturing process applied for the body structure, in particular when using a layered structure, so that a respective separator might result from a tapered area within a layer or even being provided by a respective layer. The sub-channels are preferably one over the other into the third dimension with a respective separator in-between neighboring sub-channels. The sub-channels preferably have substantially the same area into the first and second dimensions, and the respective areas into the first and second dimensions are preferably aligned to each other.

The pressure determining unit may be configured for determining pressure in a range where compressibility of the fluid becomes noticeable and/or in a range beyond 200 bar, preferably beyond 500 bar, and more preferably beyond 1000 bar.

In one embodiment, the third dimension is substantially perpendicular to the first dimension as well as is substantially perpendicular to the second dimension. Preferably, the first dimension, the second dimension, and the third dimension are all substantially perpendicular to each other.

In one embodiment, the deformation detector is or comprises a strain gauge and/or a strain gauge pressure transducer, which can be commercially available components as readily known in the art.

In one embodiment, the body structure is configured so that the fluidic path is meandering through the body structure. This may allow increasing the effective path length responsible for elongating the body structure into the second dimension.

In one embodiment, the fluidic path of the body structure comprises a plurality of first channel segments and a plurality of intermediate or second channels coupling between consecutive first channel segments.

Preferably, each first channel segment is oriented so that a direction of flow is in the first dimension.

Embodiments of the pressure determining unit according to the present invention can be applied in a separation system for separating compounds of a sample fluid in a mobile phase. The fluid separation system comprises at least a mobile phase drive and a separation unit. The mobile phase drive, preferably a pumping system, is configured to drive the mobile phase through the fluid separation system. The separation unit, preferably a chromatographic column, is configured for separating compounds of the sample fluid in the mobile phase. The pressure determining unit is then configured and applied for determining a pressure of the mobile phase. The pressure determining unit may be applied in any part of the fluidic path of the mobile phase.

The separation system may further comprise at least one of a sample dispatcher adapted to introduce the sample fluid into the mobile phase, a detector adapted to detect separated compounds of the sample fluid, a collection unit adapted to collect separated compounds of the sample fluid, a data processing unit adapted to process data received from the fluid separation system, and a degassing apparatus for degassing the mobile phase.

Embodiments of the present invention might be embodied based on most conventionally available HPLC systems, such as the Agilent 1220, 1260 and 1290 Infinity LC Series or the Agilent 1100 HPLC series (all provided by the applicant Agilent Technologies—see www.aqilent.com—which shall be incorporated herein by reference).

One embodiment of an HPLC system comprises a pumping apparatus having a piston for reciprocation in a pump working chamber to compress liquid in the pump working chamber to a high pressure at which compressibility of the liquid becomes noticeable.

One embodiment of an HPLC system comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially by 180 degrees, with respect to a liquid outlet of the second pumping apparatus, so that only one pumping apparatus is supplying into the system while the other is intaking liquid (e.g. from the supply), thus allowing to provide a continuous flow at the output. However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift. Also other types of pumps are known and operable in conjunction with the present invention.

The separating device preferably comprises a chromatographic column providing the stationary phase. The column might be a glass, metal, ceramic or a composite material tube (e.g. with a diameter from 50 μm to 5 mm and a length of 1 cm to 1 m) or a microfluidic column (as disclosed e.g. in EP 1577012 A1 or the Agilent 1200 Series HPLC-Chip/MS System provided by the applicant Agilent Technologies. The individual components are retained by the stationary phase differently and separate from each other while they are propagating at different speeds through the column with the eluent. At the end of the column they elute at least partly separated from each other. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, which can be especially chemically modified, though in EBA a fluidized bed is used.

The mobile phase (or eluent)—as the fluid—can be either a pure solvent or a mixture of different solvents. It can also contain additives, i.e. be a solution of the said additives in a solvent or a mixture of solvents. It can be chosen e.g. to adjust the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic is delivered in separate containers, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a detector for detecting separated compounds of the sample fluid, a fractionating unit for outputting separated compounds of the sample fluid, or any combination thereof. Further details of HPLC system are disclosed with respect to the aforementioned Agilent HPLC series, provided by the applicant Agilent Technologies, under www.aqilent.com which shall be incorporated herein by reference.

Embodiments of the invention can be supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanying drawing(s). Features that are substantially or functionally equal or similar will be referred to by the same reference sign(s). The illustrations in the drawings are schematic.

Referring now in greater detail to the drawings, FIG. 1 depicts a general schematic of a liquid separation system 10. A pump 20 receives a mobile phase from a solvent supply 25, typically via a degasser 27, which degases the mobile phase and thus reduces the amount of dissolved gases in it. The pump 20—as a mobile phase drive—drives the mobile phase through a separating device 30 (such as a chromatographic column) comprising a stationary phase. A sample dispatcher 40 (also referred to as sample introduction apparatus, sample injector, etc.) is provided between the pump 20 and the separating device 30 in order to subject or add (often referred to as sample introduction) portions of one or more sample fluids into the flow of a mobile phase (denoted by reference numeral 200, see also FIG. 2). The stationary phase of the separating device 30 is adapted for separating compounds of the sample fluid, e.g. a liquid. A detector 50 is provided for detecting separated compounds of the sample fluid. A fractionating unit 60 can be provided for outputting separated compounds of sample fluid.

Figure 1:
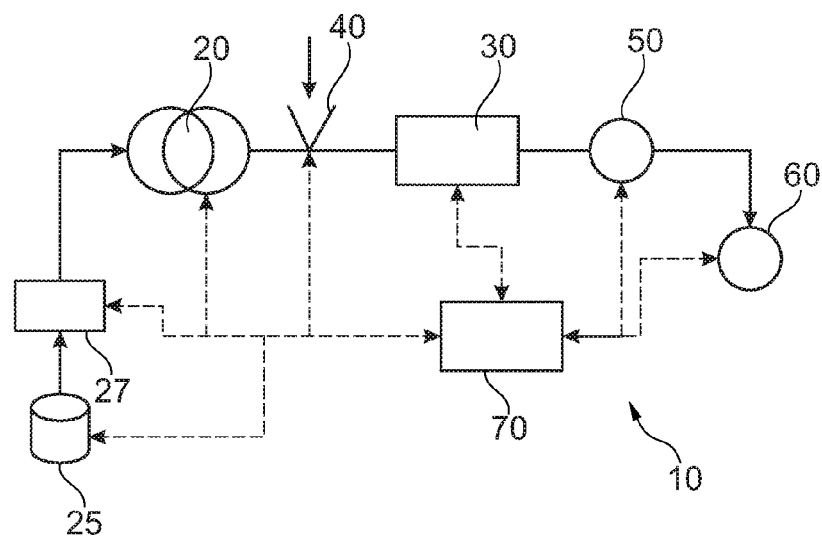
FIG. 1 shows a liquid separation system 10, in accordance with embodiments of the present invention, e.g. used in high performance liquid chromatography (HPLC).

While the mobile phase can be comprised of one solvent only, it may also be a mixture of a plurality of solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. monitoring the level or amount of the solvent available) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sample dispatcher 40 (e.g. controlling sample introduction or synchronization of the sample introduction with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back. Finally the data processing unit 70 might also process the data received from the system 10 or its part and evaluate it in order to represent it in adequate form prepared for further interpretation.

When the mobile phase propagates from the solvent supply 25 downstream towards the fractionating unit 60, the mobile phase will experience different values of pressure along the flow path. In modern HPLC systems 10, monitoring as well as controlling pressure has become increasingly important in order to achieve the requirements on performance. For that purpose, pressure sensors (also referred to as pressure determining unit) may be applied at various positions along the flow path of the mobile phase.

Figure 2A:
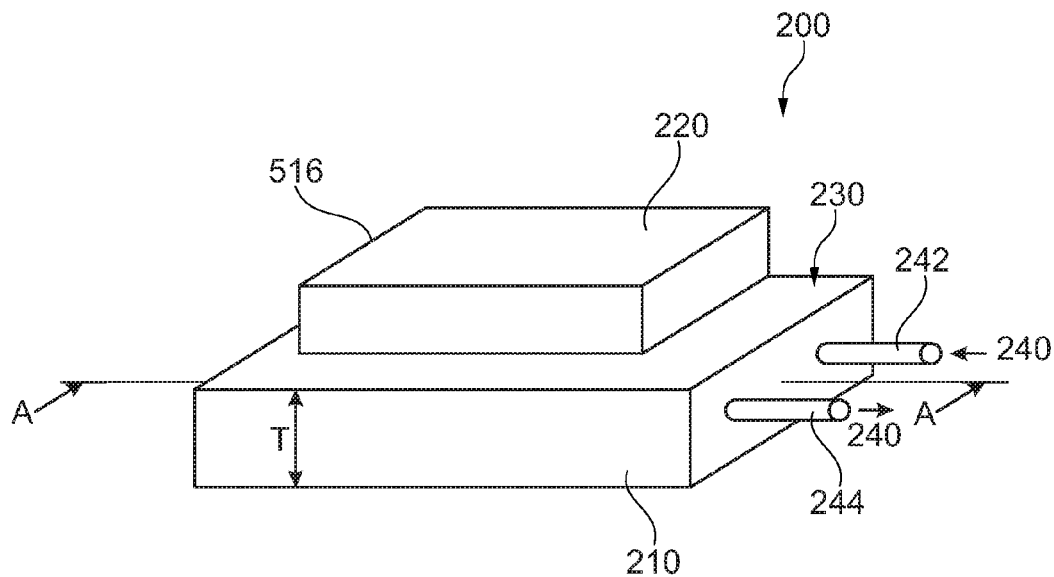
FIGS. 2A and 2B show in schematic three dimensional representation a deformation detector 200 according to the present invention.

FIG. 2A shows a schematic three dimensional representation of a deformation detector 200 according to the present invention. The pressure sensor 200 is provided by a body structure 210 bearing a strain gauge 220 on a first surface 230 (shown here as the top side of the body structure 210). As indicated by the coordinate system shown in FIG. 2, the first surface 230 of the pressure sensor 200 extends into a first direction as well as into a second direction. The pressure sensor 200 has a thickness (or height) T which extends into the third dimension.

The strain gauge pressure transducer 220 is provided and configured so that an elongation of the first surface 230 of the body structure 210 into the second dimension leads to a signal (indicated here as electrical signal SIG) corresponding to such elongation.

As will be also shown in more detail in FIG. 3, the body structure 210 provides a fluidic path 240 for conducting a fluid (such as the mobile phase in the HPLC system 10 shown in FIG. 1). The flow path 240 is indicated in FIG. 2A by respective arrows 240, and shall in this example be provided between an inlet 242 and an outlet 244. Under the influence of pressure of the fluid in the flow path 240, the body structure 210 experiences a deformation typically in each of the first, second and third dimension, whereby the degree of deformation in each of the respective dimensions is subject in particular to the specific geometry, material properties as well manufacturing process of the body structure 210. Accordingly, the pressure of the fluid in the fluidic path 240 within the body structure 210 leads to an elongation of the first surface 230 into the second dimension which, in turn, results into the signal SIG as provided by the strain gauge 220. Accordingly, the signal SIG is indicative of a value of the pressure of the fluid in the fluidic path of the body structure 210, as readily known in the art.

Figure 2B:
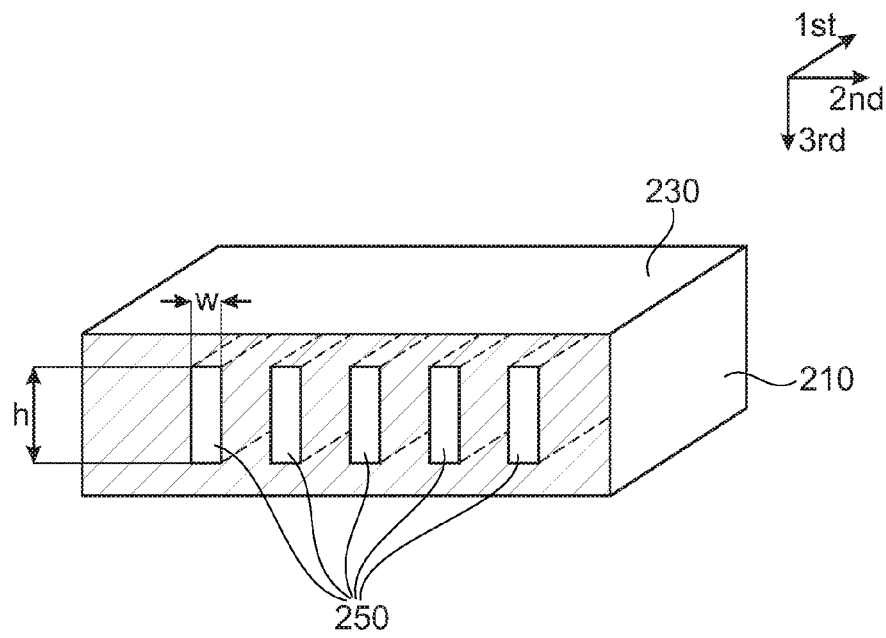

FIG. 2B shows a schematic cross-sectional view along line A-A as indicated in FIG. 2A. The cross-sectional view of FIG. 2B shows a plurality of first channel segments 250 provided within the body structure 210 and which are part of the fluidic path 240 therein. Each first channel segment 250 is oriented so that a directional flow is substantially into the first dimension. Further, each first channel segment 250 has a height h into the third dimension and a width w into the second dimension. The height h of each first channel segment 250 is designed to be at least twice of its width w. Though the first channel segments 250 in the example of the embodiment of FIG. 2B are all shown to have essentially the same geometry, other designs with different geometries are possible as well as long as the general design rule of having slim first channel segments 250 (i.e. the height h is at least twice, preferably at least three times, and more preferably at least four times, of the width w) is maintained. This design rule will be explained later in more detail. The first channel segments 250 as depicted in FIG. 2B are coupled with each other as will be shown in FIG. 3.

Figure 3A:
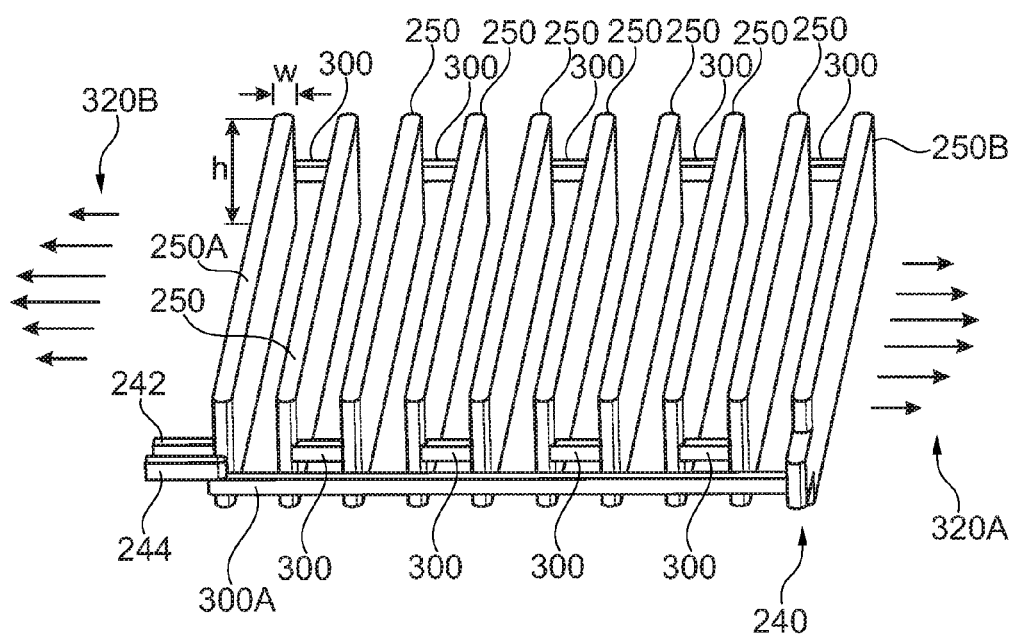
FIGS. 3A-3G illustrate embodiments of the flow path 240 as being incorporated into the body structure 210 of the pressure sensor 200.
Figure 3B:
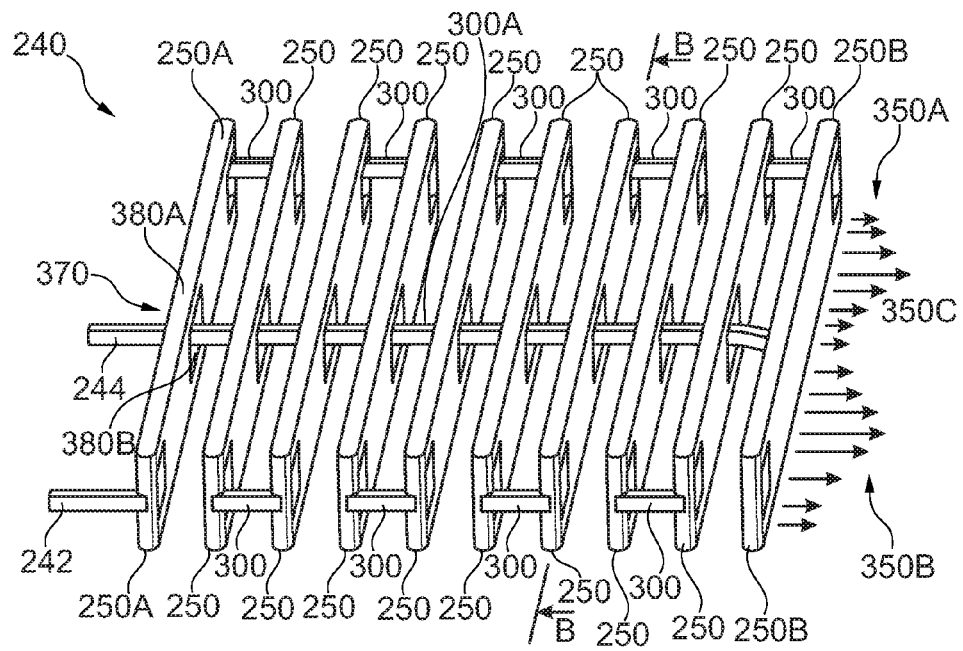

FIGS. 3A and 3B illustrate embodiments of the flow path 240 as being incorporated into the body structure 210 of the pressure sensor 200. In the three dimensional representations of FIG. 3, only the flow path 240 is shown while all other parts of the body structure 210 are omitted for the sake of simplicity. Though the flow path 240 is depicted here as solid channel structure, it is clear that the fluidic path 240 may be provided into the body structure 210 by any technology known in the art, so that the fluidic path 240 may be provided by indentations or cavities into the body structure 210.

In the embodiment of FIG. 3A, the fluidic path 240 comprises a plurality of the first channel segments 250, each being interconnected by a respective second channel segment 300. The inlet 242 is coupled to a first one 250A of the first channel segments 250, and a last one 250B of the first channel segments 250 is coupled via an extended one 300A of the second channel segments 300 to the outlet 244. It is clear that the terms inlet and outlet depend on the respective direction of flow and may also be reversed.

Under the influence of pressure in the fluid within the fluidic path 240, the first and second channel segments 250, 300 will be deformed, whereby the extent of deformation typically depends in particular on the respective geometry, material properties as well as the respective manufacturing process of the first and second channel segments 250, 300 as well as the body structure 210. However, when following the aforedescribed design requirement (see FIG. 2B) of having slim first channel segments 250, the fluidic path 240 tends to deform most into the second dimension, as indicated in FIG. 3A by arrows 320A and 320B on opposing sides of the first body structure 210. Though there also is a deformation into the first and third dimension, in the embodiments of FIG. 3 such deformation is smaller than the deformation 320A and 320B and shall be neglected here for the sake of simplicity.

The arrows 320A and 320B are represented in FIG. 3A as profile with a distribution along the first dimension. This shall indicate that the deformation 320A and 320B is typically not uniform along the first dimension but tends to be larger in particular in the middle region of first channel segments 250. Such deformation profile 320A, 320B can be influenced by the respective geometry and arrangement of the channels, which also will be explained later.

In the embodiment of FIG. 3A, the ratio of height h to width w is selected to be at least four times in order to amplify the effect of having a stronger deformation 320A, 320B into the second direction than in either one of the first and third directions. It has been found by the present inventors that such ratio can improve the performance of the pressure sensor 200.

It goes without saying that the deformation 320A, 320B, as experienced by the flow path 240, is then also transmitted into the body structure 210 leading to a deformation of the body structure 210 into the second dimension, which then can be detected by the strain gauge 220 (see FIG. 2A).

FIG. 3B shows an arrangement of the fluidic path 240 which is substantially similar to the embodiment of FIG. 3A, however, with the difference that the (e.g. return) path 300A from the last one 250B of the first segments 250 to the outlet 244 is now led in the middle and through openings 370 in the other first channel segments 250. This can also be seen by the cross-sectional view taken along lines B-B as depicted in FIG. 3C.

Figure 3C:
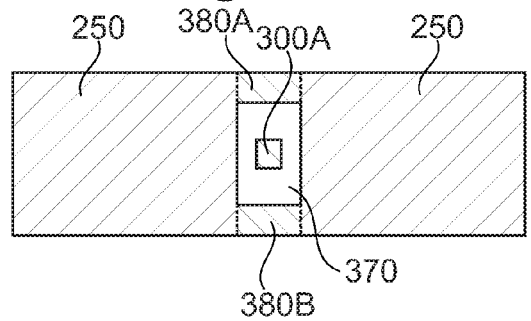

While each row into the first dimension in the embodiment of FIG. 3A is provided by only one first channel segment 250, each row in the embodiments of FIGS. 3B and 3C is provided by two first channel segments 250 arranged and coupled in a serial manner. A respective opening or intermediated area 370 is provided between such first channel segments 250 in a row. The intermediated areas 370 are not part of the fluidic path 240 or, in other words, are cut out in a respective row between neighboring first channel segments 250. In order to fluidically couple respective neighboring first channel segments 250 in a respective row, intermediate channel segments 380A and 380B are provided in the embodiment of FIG. 3C. Also shown in FIG. 3C is the first channel segment 300A being led through the respective intermediate area 370.

It is clear that the intermediate channels 380A and 380B as well as the respective first channel segments 250 in a respective row need not necessarily be different physical entities but may also be provided or manufactured as one unit and/or in one step or process. However, for the sake of better understanding, those elements are depicted as different elements in the representation of FIG. 3C.

Further in FIG. 3B is shown, again in schematic representation, a resulting deformation profile, which consists of two sub-profiles 350A and 350B. The sub-profiles 350A and 350B are shown here—the sake of simplicity—only on the right hand side but it is clear that similar profiles will also extend on the opposing left hand side.

Each of the deformation sub-profiles 350A and 350B corresponds to a respective one of the first channels 250 in a respective row, or better to say to all of the plurality of first channels 250 arranged one next to the other along the second dimension. The deformation sub-profiles 350A and 350B tend to be more evenly distributed along the first dimension in the sense that the maximum deformation in the middle (depicted as 350C) tends to be lower than the corresponding maximum deformation in the middle, for example, in an embodiment as shown in FIG. 3A which does not have respective intermediate areas 370. Though this might limit the maximum elongation resulting at the first surface 230 of the body structure 210 and thus to a reduced amplitude of the signal SIG, it has been found by the present inventors that by providing such intermediate areas 370 (and thus effectively restricting deformation in the projection of such intermediate areas 370) non-linearity effects in the resulting signal SIG of the pressure gauge 220 can be reduced.

While there can be many different embodiments with different positions and distributions of such intermediate areas 370 (e.g. which need not be aligned as shown in FIG. 3B), the embodiment of FIG. 3B has been found beneficial and leading to a significantly more linear course of the signals SIG over different values of pressure in the fluid.

Figure 3D:
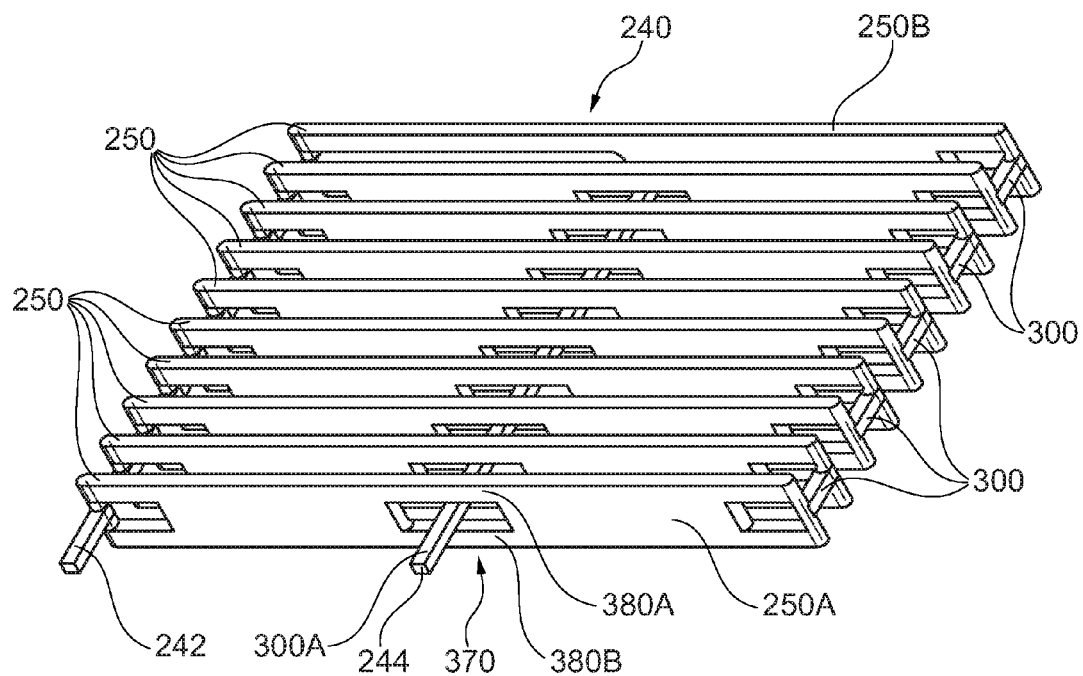
Figure 3E:
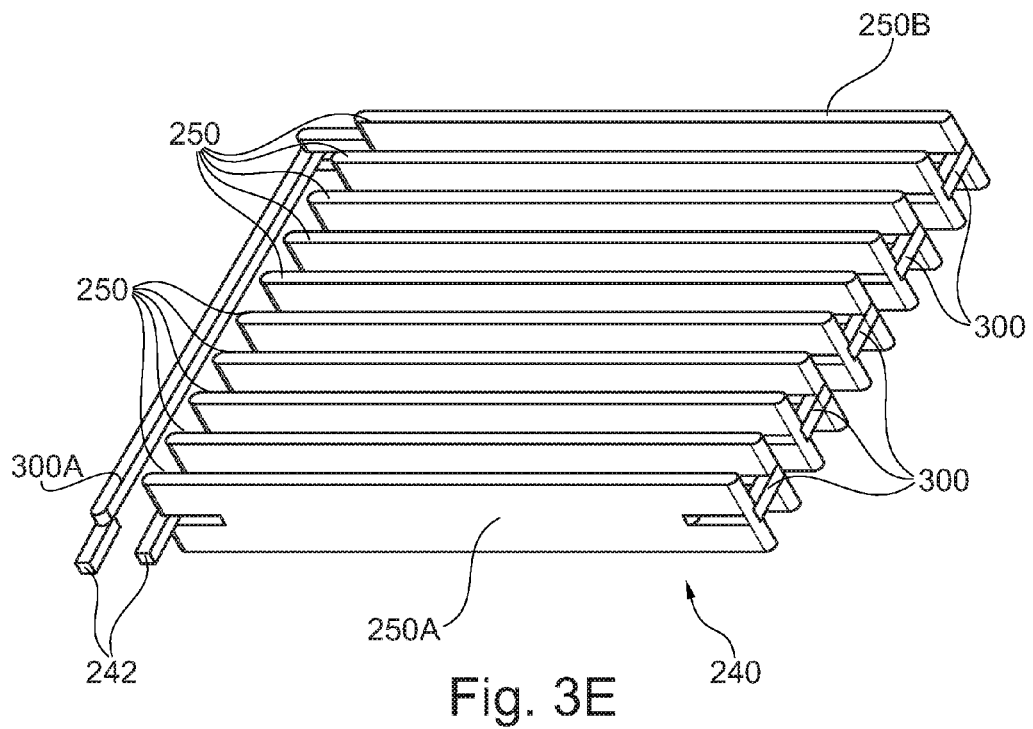
Figure 3F:
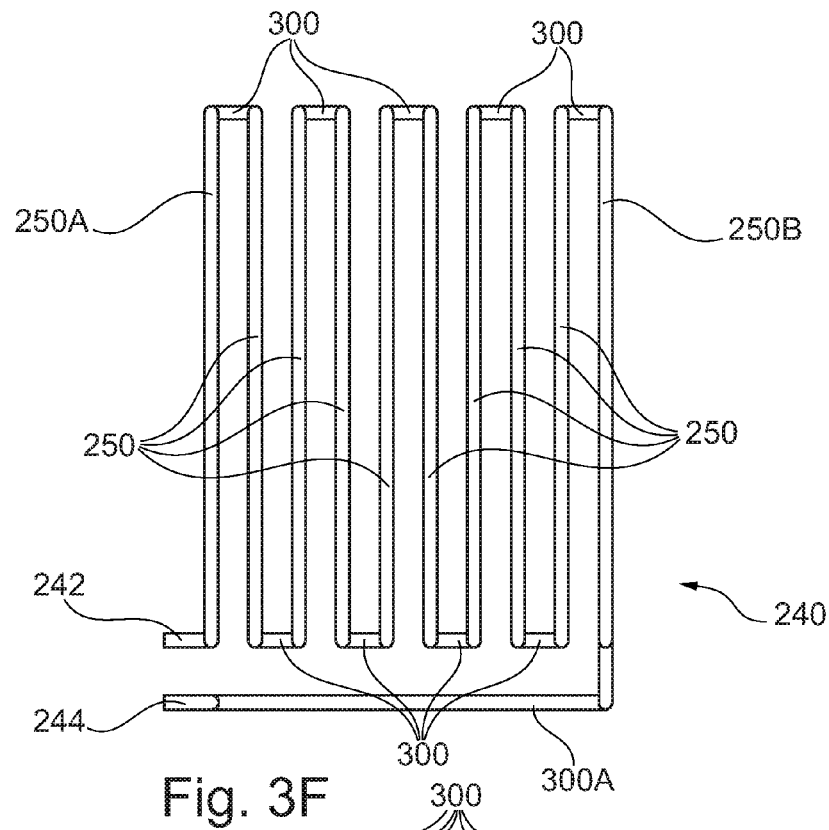
Figure 3G:
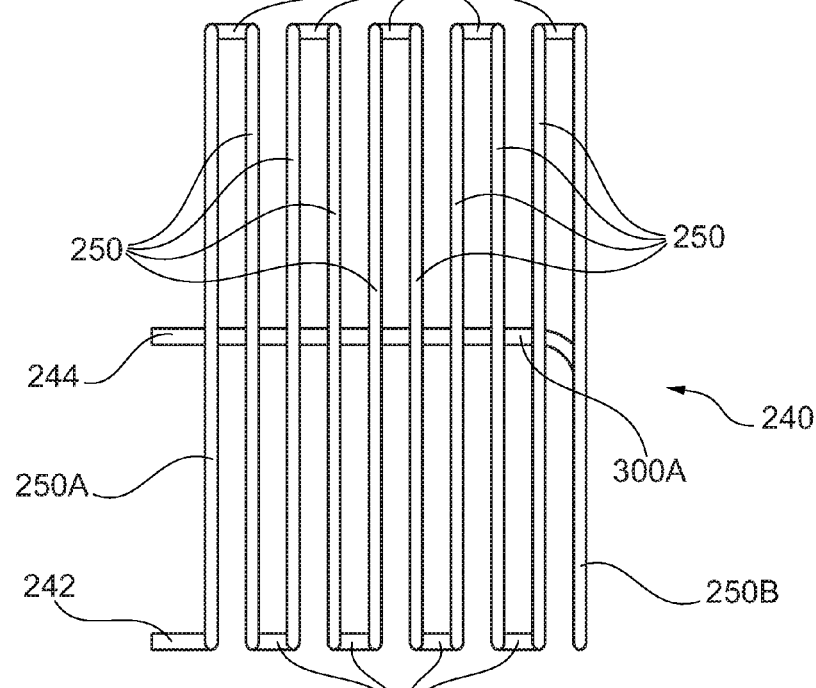

FIGS. 3D-3G show—for the sake of better visualization—additional views for the embodiments of FIGS. 3A and 3B. FIG. 3D is a three dimensional bottom view of the embodiment of FIG. 3B, and FIG. 3E is a three dimensional bottom view of the embodiment of FIG. 3A. FIG. 3F is a top view of the embodiment of FIG. 3A, and FIG. 3G is a top view of the embodiment of FIG. 3B.

Figure 4:
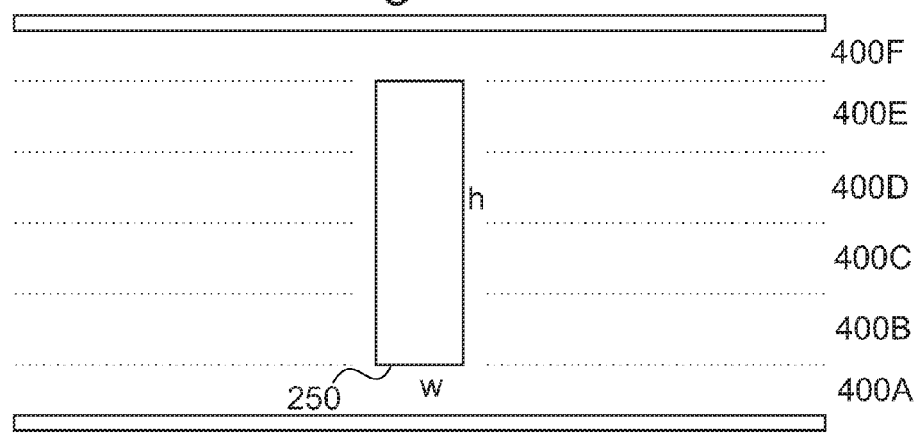
FIG. 4 shows in cross-sectional view an exemplary embodiment of a first channel segment 250 being provided by a layer arrangement.

FIG. 4 shows in a cross-sectional view (e.g. along lines A-A in FIG. 2A) an exemplary embodiment of the first channel segment 250 being provided by a layer arrangement. In this embodiment, the body structure 210 is comprised by a plurality of layers 400, e.g. metal sheets, in this example six layers 400A-400F. The first channel segment 250 can be provided by eliminating the respective area in the layers 400B-400E, for example by cutting, laser ablation, or etching, as readily known in the art. The outer layers 400A and 400F then limit the first channel segments 250 along the third axes. Though only one first channel segment 250 is depicted in FIG. 4, it goes without saying that plural such first channel segments 250 as well as corresponding second channel segments 300 can be provided in the same way dependent on the respective application.

When applying photochemical machining for removing material out of the respective layers 400, a typical process limitation can occur that a channel width cannot fall below about 1.4 (in some applications maybe down to 1.2) times the thickness of such layer. Accordingly, in order to achieve a slim geometry of the first channel segments 250, plural layers 400 each with a respective channel are stacked on top of each other thus resulting into a slim channel geometry as for example depicted in FIG. 4.

In order to improve the signal quality of signal SIG, a reference measurement may be provided, in particular in order to eliminate the influence of surface deformations on the first surface 230, in particular at regions above and/or below the respective first channel segments 250. It is clear that other effects, such as temperature dependency of the elasticity modulus, non-linear deformations within the structure, material drift of the strain gauge 220 and/or the body structure 210, may also be addressed and compensated by an adequate reference measurement.

Figure 5B:
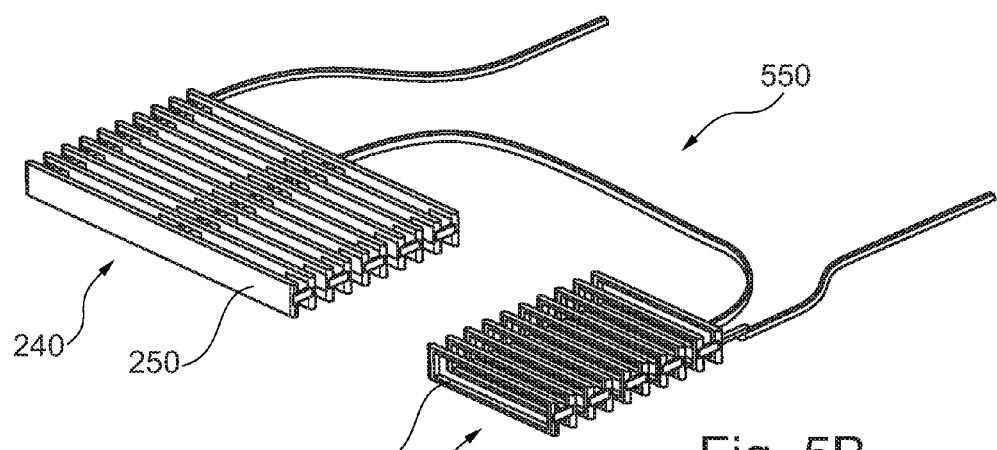
FIG. 5 illustrate embodiments of the pressure sensor 200 having a reference measurement.
Figure 5A:
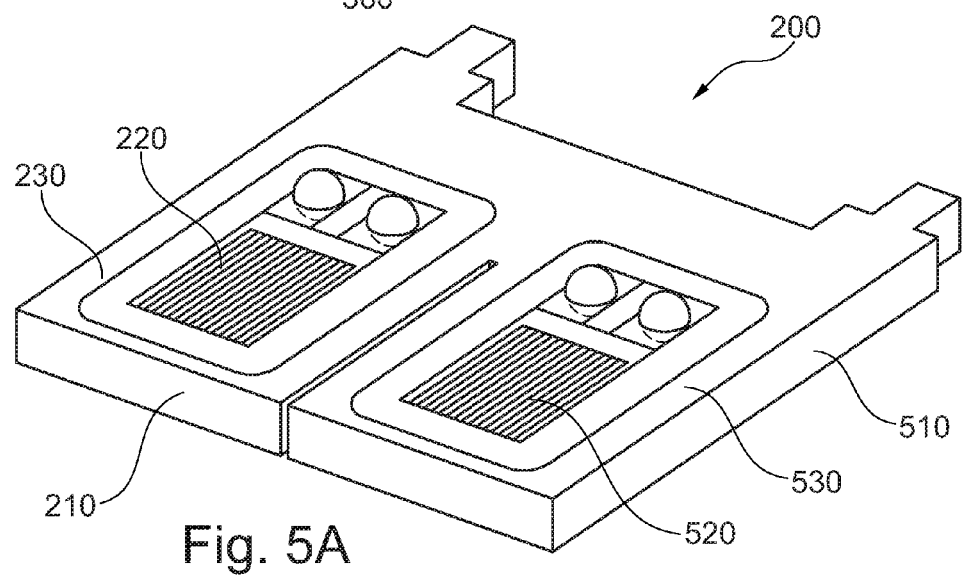

FIG. 5A shows in three dimensional representation an embodiment of the pressure sensor 200 having a reference measurement. The pressure sensor 200 comprises the body structure 210 with the strain gauge 220 positioned on its first surface 230. Further provided is a reference body structure 510 having a reference strain gauge 520 positioned on a first surface 530 of the reference body structure 510. In the embodiment of FIG. 5A, the body structure 210 together with its respective strain gauge 220 is oriented in the same way as the reference body structure 510 with its reference strain gauge 520. While this can be advantageous in particular with respect to the manufacturing process (e.g. allowing to provide both in one manufacturing step or sequence of steps), it is clear that the body structure 210 and the reference body structure 510 might also be provided as fully independent components and being oriented fully independent of each other.

The reference strain gauge 520 generates a reference signal RSIG (not shown in the Figs.) indicative of a value of the pressure of the fluid in the reference body structure 510.

FIG. 5B shows (in three dimensional representation similar to FIGS. 3A and 3B) a fluidic path 550 through both of the body structure 210 and the reference body structure 510. In the embodiment of FIG. 5B the fluidic path 240 through the body structure 210 substantially corresponds to the embodiment shown in FIG. 3B, which is then coupled in serial connection to a fluidic path 560 of the reference body structure 510.

Figure 5C:
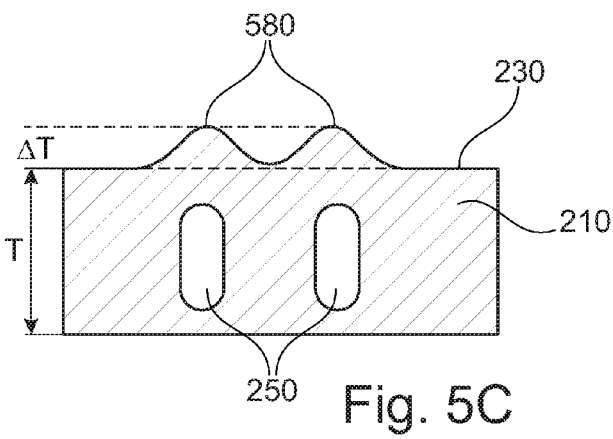

FIG. 5C schematically illustrates (e.g. along lines A-A in FIG. 2A) the effect of a three dimensional deformation of the first surface 230 (and correspondingly of the first of the reference body structure 510). Under the influence of pressure of the fluidic in the fluidic path 240, the first channel segments 250 also exhibit a deformation into the third dimension which may then result into deformations 580 of the first surface 230 (i.e. a variation $\Delta T$ in the thickness T). Such deformations 580 can lead to an error in the signal SIG by also inducing deformation into the second dimension. It is clear that the type of surface deformation as depicted in FIG. 5C also applies, mutatis mutandis, to the reference body structure 510 and its first surface 530. FIG. 5C only shows the deformation into the third dimension while any other deformation is omitted for the sake of simplicity.

In order to remove or at least reduce effects resulting from surface deformations on the first surface 230, the reference body structure 510 is configured so that its (three dimensional) pattern of variation $\Delta T$ in this thickness T of its first surface 530 of the reference body structure 510 substantially matches to a (three dimensional) pattern of variation in thickness of the body structure 210 on its first surface 230 under the influence of a variation in pressure in the fluid path. This can be accomplished by designing the channel geometry of the reference body structure 510 so that the respective width w of the channels corresponding to the first channel segments 250 as well as their spatial distribution into the second dimension substantially matches with the body structure 210. At the same time, the respective height of the channels in the reference body structure 510 is designed to be as small as possible, so that under the influence of pressure the reference body structure 510 mainly exhibits the deformation 580 in its thickness $\Delta T$ rather than being elongated into the second dimension.

Figure 5D:
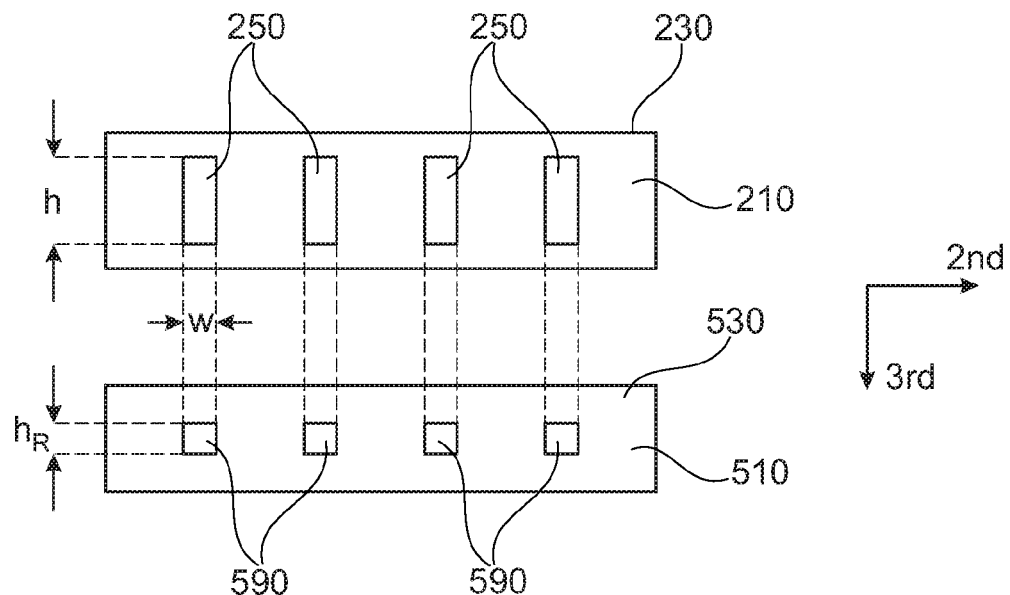

FIG. 5D illustrates schematically (e.g. along lines A-A in FIG. 2A) the design of the relevant channels in the reference body structure 510 with respect to the body structure 210. The reference body structure 510 comprises a plurality of channels 590 which correspond to the first channel segments 250 in respect to their spatial distribution within the respective body structures 210 and 510. Also, the width w of both the first channel segments 250 and the channel segments 590 are designed to be substantially the same. However, a height $h_R$ of the reference channel segments 590 is designed to be significantly smaller than the height h of the first channel segments 250. In the example of FIG. 5D, the height $h_R$ substantially corresponds to the width w. With such design, the reference body structure 510 exhibits substantially the same deformation pattern on its first surface 530 into the third dimension than the body structure 210, whereas any deformation of the reference body structure 510 into the second dimension is designed to be significantly smaller than any deformation of the body structure 210 into the second dimension at the same applied pressure of the fluid.

The signal SIG and the reference signal RSIG are then analyzed together, preferably by either subtracting both signals in an adequate data processing unit (such as the data processing unit 70 as depicted in FIG. 1) or e.g. in an adequate electronic circuitry such as a Wheatstone bridge as readily known in the art.

Figure 6:
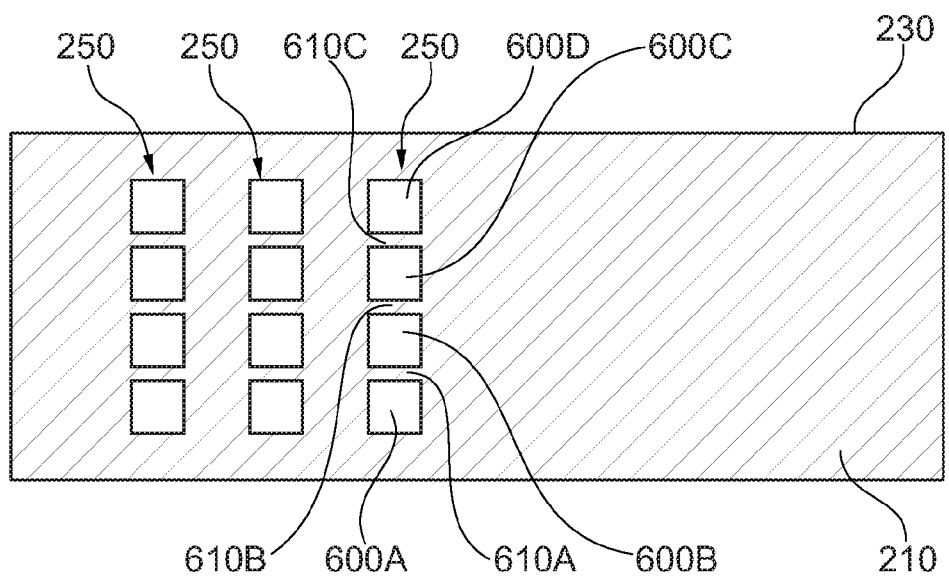
FIG. 6 illustrates in schematic cross-sectional view an embodiment wherein each first channel segment 250 is provided by a plurality of first sub-channels 600.

FIG. 6 illustrates in schematic cross-sectional view (e.g. along line A-A of FIG. 2A) an embodiment wherein each first channel segment 250 is provided by a plurality of first sub-channels 600, in the embodiment here by four first sub-channels 600A-600D. The first sub-channels 600A-600D are arranged in a parallel configuration (with respect to the third dimension) and each two neighboring first sub-channels 600 having a respective separator 610 in-between. In the embodiment of FIG. 6, a separator 61 OA is provided between the first sub-channels 600A and 600B, a separator 610B is provided between the first sub-channels 600B and 600C, and a separator 610C is provided between the first sub-channels 600C and 600D. Each separator 610 may be a membrane, providing a certain degree of pressure communication between neighboring first sub-channels 600, or any other kind of more or less rigid separation. In case the first body structure 210 is provided by a layered structure, each respective separator 610 might result from a tapered area within a layer or even be provided by a respective layer. In the embodiment of FIG. 6, the respective first sub-channels 600A-600D providing a respective first channel segment 250 are preferably arranged one over the other into the third dimension with the respective separator 610 in-between neighboring first sub-channels 600. Further in the embodiment of FIG. 6, the first sub-channels 600 are designed to have substantially the same area into the first and second dimensions.

Though the first channel segments 250 in the aforede-scribed embodiments are shown as all having the same geometry (i.e. height and width), it is clear that the geometry might also vary between the first channel segments 250. Also, it is not necessary that all of the first channel segments 250 fulfill the slim channel geometry. However, increasing the number of first channel segments 250 fulfilling the slim channel geometry might allow increasing the degree of deformation of the first surface 230 into the second dimension. Further, while the first channel segments 250 in the aforedescribed embodiments are all oriented to extend straight into the first direction and thus all oriented substantially in parallel to each other, it is clear that not all of the first channel segments 250 necessarily need to have the same orientation and one or more of the first channel segments 250 might also extend along the second and/or the third dimension. The straight rectangular geometry of the afore-described embodiments is used and shown for the sake of simplicity and easier understanding only.

The invention claimed is:

1. A pressure determining unit configured for determining a pressure of a fluid, the pressure determining unit comprising:
   a body structure comprising a fluidic path configured for conducting the fluid, wherein the body structure has a first surface in a first dimension and in a second dimension, and a thickness in a third dimension, and
   a deformation detector configured for responding to an elongation into the second dimension of the first surface of the body structure by generating a signal indicative of a value of the pressure of the fluid in the body structure,
   wherein the fluidic path of the body structure comprises one or more first channel segments, each first channel segment having a height into the third dimension being at least twice its width into the second dimension.

2. The pressure determining unit of claim 1, wherein each first channel segment has a height into the third dimension being at least three times its width into the second dimension.

3. The pressure determining unit of claim 1, comprising at least one of:
   the plurality of first channel segments are oriented so that a direction of flow is substantially in the first dimension;
   at least two of the first channel segments are arranged in a respective row along the first dimension and having a respective intermediate area between neighboring channel segments arranged in the respective row, which intermediate area is not part of the fluidic path;
   the fluidic path comprises a plurality of respective rows along the first dimension, and a plurality of second channel segments each oriented so that a direction of flow is substantially in the second dimension, wherein at least one of the second channel segments is surrounded by at least one intermediate area, wherein preferably each row along the first dimension comprises two channel segments and has a respective intermediate area between two channel segments, each row along the first dimension is coupled by a respective second channel segment, and the last row is further coupled to a respective second channel segment which is respectively surrounded by the respective intermediate areas of the rows.

4. A pressure determining unit configured for determining a pressure of a fluid, the pressure determining unit comprising:
   a body structure comprising a fluidic path configured for conducting the fluid, wherein the body structure has a first surface in a first dimension and in a second dimension, and a thickness in a third dimension, and
   a deformation detector configured for responding to an elongation into the second dimension of the first surface of the body structure by generating a signal indicative of a value of the pressure of the fluid in the body structure, wherein:
   the fluidic path of the body structure comprises a plurality of first channel segments oriented so that a direction of flow is substantially in the first dimension, and
   at least two of the first channel segments are arranged in a respective row along the first dimension and having a respective intermediate area between neighboring channel segments arranged in the respective row, wherein the intermediate area is not part of the fluidic path.

5. The pressure determining unit of claim 4, wherein:
   the fluidic path comprises a plurality of respective rows along the first dimension, and
   a plurality of second channel segments each oriented so that a direction of flow is substantially in the second dimension, wherein at least one of the second channel segments is surrounded by at least one intermediate area.

6. The pressure determining unit of claim 4, wherein:
   each row along the first dimension comprises two channel segments of said first channel segments and has a respective intermediate area between two channel segments,
   each row along the first dimension is coupled together by a respective second channel segment, and
   the last row is further coupled to a respective second channel segment which is respectively surrounded by the respective intermediate areas of the rows.

7. A pressure determining unit configured for determining a pressure of a fluid, the pressure determining unit comprising:
   a body structure comprising a fluidic path configured for conducting the fluid, wherein the body structure has a first surface in a first dimension and in a second dimension, and a thickness in a third dimension:
   a deformation detector configured for responding to an elongation into the second dimension of the first surface of the body structure by generating a signal indicative of a value of the pressure of the fluid in the body structure;

a reference body structure comprising a reference fluidic path configured for conducting the fluid, wherein the reference body structure has a first surface in a first dimension and in a second dimension, and a thickness in a third dimension; and a reference deformation detector configured for responding to an elongation into the second dimension of the first surface of the reference body structure by generating a reference signal indicative of a value of the pressure of the fluid in the reference body structure, wherein:

the fluidic path and the reference fluidic path are fluidically coupled with each other, and the reference body structure is configured to have a pattern of variation in thickness on its first surface under the influence of a variation in pressure in the reference fluid path, which substantially matches to a pattern of variation in thickness of the body structure on its first surface under the influence of a variation in pressure in the fluid path.

8. The pressure determining unit of claim 7, comprising at least one of:

a signal processing unit for deriving a value of the pressure of the fluid by jointly analyzing the signal and the reference signal;

the fluidic path of the body structure comprises one or more first channel segments, each first channel segment having a width into the second dimension and the reference fluidic path of the reference body structure comprises one or more first reference channel segments, each first reference channel segment having a width into the second dimension, wherein the width of the first channel segments corresponds to the width of the first reference channel segments;

the fluidic path of the body structure comprises one or more first channel segment, each first channel segment having a height into the third dimension, and the reference fluidic path of the reference body structure comprises one or more first reference channel segments, each first reference channel segment having a height into the third dimension, wherein the height of the first channel segments is at least twice the height of the first reference channel segments.

9. The pressure determining unit of claim 7, comprising at least one of:

each first channel segment has a height into the third dimension being at least twice its width into the second dimension;

the at least one first channel segment comprises a plurality of first channel segments are oriented so that a direction of flow is substantially in the first dimension;

at least two of the first channel segments are arranged in a respective row along the first dimension and having a respective intermediate area between neighboring channel segments arranged in the respective row, which intermediate area is not part of the fluidic path;

the fluidic path comprises a plurality of respective rows along the first dimension, and a plurality of second channel segments each oriented so that a direction of flow is substantially in the second dimension, wherein at least one of the second channel segments is surrounded by at least one intermediate area, wherein each row along the first dimension comprises two channel segments of the at least one channel segment and has a respective intermediate area between two channel segments, each row along the first dimension is coupled by a respective second channel segment, and the last row is further coupled to a respective second channel segment which is respectively surrounded by the respective intermediate areas of the rows.

10. The pressure determining unit of claim 1, comprising at least one of:

the body structure comprises a plurality of layers laminated to one another;

the body structure comprises a plurality of layers laminated to one another, wherein the layers are elongated into the first dimension and into the second dimension, and each layer has a thickness into the third dimension being significantly smaller than the respective elongations into the first dimension and into the second dimension;

the body structure is comprised of one or more materials of a group of materials comprising: metal, ceramic, polymer, composite material;

the body structure comprises a plurality of layers, each layer being a material selected from the group consisting of: metal, ceramic, polymer, and composite material;

at least one channel segment is comprised of a plurality of sub-channels arranged in parallel and having a respective separator between neighboring sub-channels.

11. The pressure determining unit of claim 1, comprising at least one of:

the pressure determining unit is configured for determining pressure in a range where compressibility of the fluid becomes noticeable;

the pressure determining unit is configured for determining pressure in a range beyond 200 bar, or beyond 500 bar, or beyond 1000 bar;

the third dimension is substantially perpendicular to the first dimension and to the second dimension;

the first dimension, the second dimension, and the third dimension are substantially perpendicular to each other;

the deformation detector is or comprises one of a strain gauge and a strain gauge pressure transducer.

12. The pressure determining unit of claim 1, comprising at least one of:

the fluidic path is meandering through the body structure;

the fluidic path of the body structure comprises a plurality of the first channel segments and a plurality of intermediate channels coupling between consecutive first channel segments;

each first channel segment is oriented so that a direction of flow is in the first dimension.

13. A fluid separation system for separating compounds of a sample fluid in a mobile phase, the fluid separation system comprising:

a mobile phase drive adapted to drive the mobile phase through the fluid separation system, a separation unit adapted for separating compounds of the sample fluid in the mobile phase, and the pressure determining unit of claim 1 configured for determining a pressure of the mobile phase.

14. The fluid separation system of claim 13, further comprising at least one of:

a sample dispatcher adapted to introduce the sample fluid into the mobile phase;

a detector adapted to detect separated compounds of the sample fluid;

a collection unit adapted to collect separated compounds of the sample fluid;
a data processing unit adapted to process data received from the fluid separation system;
a degassing apparatus for degassing the mobile phase.

15. The pressure determining unit of claim 1, comprising:
a reference body structure comprising a reference fluidic path configured for conducting the fluid, wherein the reference body structure has a first surface in a first dimension and in a second dimension, and a thickness in a third dimension; and
a reference deformation detector configured for responding to an elongation into the second dimension of the first surface of the reference body structure by generating a reference signal indicative of a value of the pressure of the fluid in the reference body structure,
wherein the fluidic path and the reference fluidic path are fluidically coupled with each other, and the reference body structure is configured to have a pattern of variation in thickness on its first surface under the influence of a variation in pressure in the reference fluid path, which substantially matches to a pattern of variation in thickness of the body structure on its first surface under the influence of a variation in pressure in the fluid path.

16. The pressure determining unit of claim 15, comprising at least one of:
a signal processing unit for deriving a value of the pressure of the fluid by jointly analyzing the signal and the reference signal;
the fluidic path of the body structure comprises one or more first channel segments, each first channel segment having a width into the second dimension, and the reference fluidic path of the reference body structure comprises one or more first reference channel segments, each first reference channel segment having a width into the second dimension, wherein the width of the first channel segments corresponds to the width of the first reference channel segments;
the fluidic path of the body structure comprises one or more first channel segments, each first channel segment having a height into the third dimension, and the reference fluidic path of the reference body structure comprises one or more first reference channel segments, each first reference channel segment having a height into the third dimension, wherein the height of the first channel segments is at least twice the height of the first reference channel segments.

17. The pressure determining unit of claim 4, comprising:
a reference body structure comprising a reference fluidic path configured for conducting the fluid, wherein the reference body structure has a first surface in a first dimension and in a second dimension, and a thickness in a third dimension; and
a reference deformation detector configured for responding to an elongation into the second dimension of the first surface of the reference body structure by generating a reference signal indicative of a value of the pressure of the fluid in the reference body structure,
wherein the fluidic path and the reference fluidic path are fluidically coupled with each other, and the reference body structure is configured to have a pattern of variation in thickness on its first surface under the influence of a variation in pressure in the reference fluid path, which substantially matches to a pattern of variation in thickness of the body structure on its first surface under the influence of a variation in pressure in the fluid path.

18. The pressure determining unit of claim 17, comprising at least one of:
a signal processing unit for deriving a value of the pressure of the fluid by jointly analyzing the signal and the reference signal;
the fluidic path of the body structure comprises one or more first channel segments, each first channel segment having a width into the second dimension, and the reference fluidic path of the reference body structure comprises one or more first reference channel segments, each first reference channel segment having a width into the second dimension, wherein the width of the first channel segments corresponds to the width of the first reference channel segments;
the fluidic path of the body structure comprises one or more first channel segments, each first channel segment having a height into the third dimension, and the reference fluidic path of the reference body structure comprises one or more first reference channel segments, each first reference channel segment having a height into the third dimension, wherein the height of the first channel segments is at least twice the height of the first reference channel segments.

* * * * *